(12) United States Patent
Huet et al.

(10) Patent No.: US 7,674,299 B2
(45) Date of Patent: Mar. 9, 2010

(54) DIRECT DYE COMPOSITION COMPRISING A CATIONIC SURFACTANT, A BIOHETEROPOLYSACCHARIDE, AN AMPHOTERIC SURFACTANT AND DIRECT DYE

(75) Inventors: Nathalie Huet, Paris (FR); Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/003,329

(22) Filed: Dec. 21, 2007

(65) Prior Publication Data

US 2008/0313820 A1    Dec. 25, 2008

Related U.S. Application Data

(60) Provisional application No. 60/881,141, filed on Jan. 19, 2007.

(30) Foreign Application Priority Data

Dec. 21, 2006    (FR) .................................. 06 55808

(51) Int. Cl.
    *A61Q 5/10*    (2006.01)
(52) U.S. Cl. ...................... 8/405; 8/426; 8/435; 8/463; 8/552; 8/594; 8/606
(58) Field of Classification Search .................... 8/405, 8/426, 435, 463, 552, 594, 606
    See application file for complete search history.

(56) References Cited

U.S. PATENT DOCUMENTS

| | | | |
|---|---|---|---|
| 2,528,378 | A | 10/1950 | Mannheimer et al. |
| 2,781,354 | A | 2/1957 | Mannheimer et al. |
| 4,137,180 | A | 1/1979 | Naik et al. |
| 4,834,768 | A | 5/1989 | Grollier |
| 4,874,554 | A | 10/1989 | Lange et al. |
| 4,904,275 | A * | 2/1990 | Grollier .......... 8/408 |
| 5,061,289 | A | 10/1991 | Clausen et al. |
| 5,196,029 | A | 3/1993 | Kawase et al. |
| 5,380,340 | A | 1/1995 | Neunhoeffer et al. |
| 5,708,151 | A | 1/1998 | Möckli |
| 5,766,576 | A | 6/1998 | Löwe et al. |
| 6,099,592 | A | 8/2000 | Vidal et al. |
| 6,099,593 | A | 8/2000 | Terranova et al. |
| 6,270,533 | B1 | 8/2001 | Genet et al. |
| 6,340,371 | B1 | 1/2002 | Genet et al. |
| 6,377,398 | B1 | 4/2002 | Pieri et al. |
| 6,565,614 | B1 | 5/2003 | Genet et al. |
| 6,638,321 | B1 | 10/2003 | Genet et al. |
| 6,660,046 | B1 | 12/2003 | Terranova et al. |
| 6,730,789 | B1 | 5/2004 | Birault et al. |
| 6,783,557 | B1 | 8/2004 | Terranova et al. |
| 7,402,180 | B2 | 7/2008 | Vuarier et al. |
| 2003/0150069 | A1 * | 8/2003 | Kleen et al. ........... 8/561 |
| 2004/0025266 | A1 * | 2/2004 | Cottard et al. .......... 8/405 |

FOREIGN PATENT DOCUMENTS

| | | |
|---|---|---|
| DE | 2 359 399 A1 | 6/1975 |
| DE | 3 843 892 A1 | 6/1990 |
| DE | 4 133 957 A1 | 4/1993 |
| DE | 195 43 988 A1 | 5/1997 |
| DE | 200 11 145 U1 | 10/2001 |
| EP | 0 714 954 A2 | 6/1996 |
| EP | 0 770 375 A1 | 5/1997 |
| EP | 1 142 561 A1 | 10/2001 |
| EP | 1 224 927 A1 | 7/2002 |
| EP | 1 234 569 A1 | 8/2002 |
| EP | 1 279 395 A1 | 1/2003 |
| EP | 1 348 695 A1 | 10/2003 |
| EP | 1 559 403 A1 | 8/2005 |
| EP | 1 716 841 A1 | 11/2006 |
| EP | 1 820 491 A1 | 8/2007 |
| FR | 2 548 895 A1 | 1/1985 |
| FR | 2 575 067 A1 | 6/1986 |
| FR | 2 733 749 A1 | 11/1996 |
| FR | 2 750 048 A1 | 12/1997 |
| FR | 2 766 177 A1 | 1/1999 |
| FR | 2 766 178 A1 | 1/1999 |
| FR | 2 766 179 A1 | 1/1999 |
| FR | 2 782 716 A1 | 3/2000 |
| FR | 2 782 718 A1 | 3/2000 |
| FR | 2 782 719 A1 | 3/2000 |
| FR | 2 788 521 A1 | 7/2000 |
| FR | 2 788 522 A1 | 7/2000 |
| FR | 2 801 308 A1 | 5/2001 |
| FR | 2 837 821 A1 | 10/2003 |
| GB | 1 026 978 | 4/1966 |
| GB | 1 153 196 | 5/1969 |
| JP | 2-19576 A | 1/1990 |
| JP | 5-163124 | 6/1993 |
| JP | 2526099 | 8/1996 |
| WO | WO 94/08969 A1 | 4/1994 |
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 01/78668 A1 | 10/2001 |

OTHER PUBLICATIONS

"Handbook of Surfactants" by M.R. Porter, published by Blackie & Son (Glasgow and London), 1991, pp. 116-178).

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a composition for dyeing keratin fibers, comprising at least one direct dye, at least one bioheteropolysaccharide, at least one cationic surfactant and at least one amphoteric or non-ionic surfactant. Such a composition makes it possible to obtain compositions that allow intense and relatively nonselective shades to be obtained, leaving the hair with good cosmetic properties.

17 Claims, No Drawings

OTHER PUBLICATIONS

English language Derwent abstract for DE 2359399 A1, (1975).
English language Derwent abstract for DE 200 11 145 U1, (2001).
English language Derwent abstract for EP 0770375 A1, (1997).
English language Derwent abstract for EP 1224927 A1, (2002).
English language Derwent abstract for EP 1348695 A1, (2003).
English language Derwent abstract for EP 1716841 A1, (2006).
English language Derwent abstract for FR 2782716 A1, (2000).
English language Derwent abstract for FR 2837821 A1, (2003).
English language Derwent abstract for JP 2-19576 A, (1990).
English language Derwent abstract for JP 2526099, (1996).
English language Derwent abstract for JP 5-163124, (1993).
English language abstract for WO 94/08969 A1, (1994).
English language abstract for WO 94/08970 A1, (1994).
English language abstract for WO 96/15765 A1, (1996).
English language abstract for WO 01/78668 A1, (2001).
Co-Pending U.S. Appl. No. 12/000,890; Title: Oxidation Dye Composition Containing a Cationic Surfactant, a Bioheteropolysaccharide, an Amphoteric Surfactant, and a Dye Precursor; filed Dec. 18, 2007.
Office Action in co-pending U.S. Appl. No. 12/000,890 dated Nov. 19, 2008.
French Search Report for French Application No. 0655808 (French priority application for the present application) dated Sep. 10, 2007.
French Search Report for French Application No. 0655806 (French priority application for U.S. Appl. No. 12/000,890) dated Sep. 7, 2007.
Office Action in co-pending U.S. Appl. No. 12/000,890 dated Jun. 26, 2009.

* cited by examiner

DIRECT DYE COMPOSITION COMPRISING A CATIONIC SURFACTANT, A BIOHETEROPOLYSACCHARIDE, AN AMPHOTERIC SURFACTANT AND DIRECT DYE

This application claims benefit of U.S. Provisional Application No. 60/881,141, filed Jan. 19, 2007, the contents of which are incorporated herein by reference. This application also claims benefit of priority under 35 U.S.C. § 119 to French Patent Application No. FR 06 55808, filed Dec. 21, 2006, the contents of which are also incorporated herein by reference.

The present disclosure relates to a composition for the direct dyeing of keratin fibers, such as human keratin fibers.

It is a known practice to dye keratin fibers, such as human hair, with dye compositions containing direct dyes, such as nitrobenzene dyes, acidic azo dyes, cationic azo dyes, anthraquinone dyes, or natural dyes.

These colorations may be carried out by direct application of the composition containing the direct dye(s) to the keratin fibers, or by application of an extemporaneously prepared mixture of a composition containing the direct dye(s) with a composition containing an oxidizing, bleaching agent, such as aqueous hydrogen peroxide. In the latter case, this process is referred to generally as lightening direct dyeing.

It is a known practice to prepare compositions for the direct dyeing of keratin fibers, such as human keratin fibers, by combining the direct dyes with surfactants and/or thickeners in order to improve the physical properties and/or the colorations obtained on the keratin fibers.

Compositions comprising a direct dye and a xanthan gum used to obtain better thickening of the direct dye compositions are described in, for example, French Patent FR 2 548 893. These compositions may also contain surfactants.

However, the compositions described above do not always give entirely satisfactory cosmetic and/or dyeing properties. For example, the intensity of the colorations and their selectivities representative of color differences between various parts of one or more hairs according to the degree of sensitization may not be satisfactory.

Thus, it would be desirable to develop novel compositions for the direct dyeing of keratin fibers, such as the hair, which may make it possible to overcome at least one of these drawbacks. In particular, it would be desirable to obtain compositions which may make it possible to obtain intense and relatively nonselective shades, while still leaving the hair with good cosmetic properties.

Thus, the present disclosure relates to a composition for dyeing keratin fibers, comprising at least one direct dye, at least one bioheteropolysaccharide, at least one cationic surfactant, and at least one amphoteric or nonionic surfactant.

In the composition of the present disclosure, the at least one direct dye may be chosen from any of the direct dyes known in the art for dyeing keratin fibers, such as the hair.

The at least one direct dye that can be used according to the present disclosure is chosen from, for example, neutral, acidic, or cationic nitrobenzene direct dyes, neutral, acidic, or cationic azo direct dyes, neutral, acidic, or cationic quinone, such as anthraquinone, direct dyes, azine direct dyes, triarylmethane direct dyes, indoamine direct dyes, and natural direct dyes.

Among the benzene-based direct dyes that can be used according to the present disclosure, mention may be made, in a non-limiting manner, of the following compounds:
1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitro-benzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl- 2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene; and
1-hydroxy-4-β-hydroxyethylamino-3-nitrobenzene.

The azo direct dyes that can be used according to the present disclosure may be chosen from the cationic azo dyes described in International Patent Applications WO 95/15144 and WO 95/01772, and European Patent EP 714 954, the content of which is incorporated herein by reference.

Among these azo direct dyes, in at least one embodiment mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulphate.

Other non-limiting examples of azo direct dyes, include those dyes described in the Colour Index International 3rd edition:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;

Acid Orange 24; and

Disperse Black 9.

Non-limiting mention may also be made of 1-(4'-aminodiphenylazo)-2-methyl-4-bis(β-hydroxyethyl)aminobenzene and 4-hydroxy-3-(2-methoxyphenylazo)-1-naphthalenesulphonic acid.

Non-limiting examples of quinone direct dyes include:

Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99;
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone; and
1,4-bis(β,γ-dihydroxypropylamino)anthraquinone.

Non-limiting examples of azine direct dyes include:

Basic Blue 17 and
Basic Red 2.

Non-limiting examples of triarylmethane direct dyes that can be used according to the present disclosure include the following compounds:

Basic Green 1;
Acid Blue 9;
Basic Violet 3;
Basic Violet 14;
Basic Blue 7;
Acid Violet 49;
Basic Blue 26; and
Acid Blue 7.

Non-limiting examples of indoamine direct dyes that can be used according to the present disclosure include the following compounds:

2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine; and
3-[4'-N-(ethyl,carbamylmethyl)amino]phenylureido-6-methyl-1,4-benzoquinoneimine.

Non-limiting examples of natural direct dyes that can be used according to the present disclosure may be chosen from lawsone, juglone, alizarine, purpurine, carminic acid, kermesic acid, purpurogallin, protocatechaldehyde, indigo, isatin, curcumin, spinulosin, and apigenidin. Extracts or decoctions containing these natural direct dyes, such as henna-based poultices or extracts, may also be used.

The direct dyes may be fluorescent. Non-limiting examples of fluorescent dyes include compounds having the following structures (I) or (II):

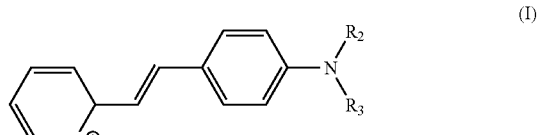

(I)

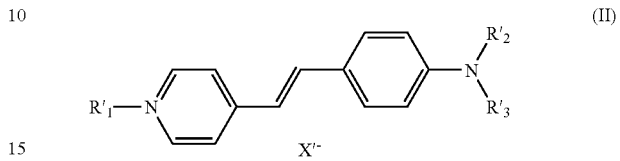

(II)

wherein $R_1$, $R_2$, $R_3$, $R'_1$, $R'_2$, and $R'_3$ are each a $C_1$-$C_{10}$ radical, for example a $C_1$-$C_4$ alkyl radical; and $X^-$ is a counterion of an inorganic and/or organic acid.

The amount of the at least one direct dye ranges from 0.001% to 20% by weight of the total weight of the composition, for example ranging from 0.005% to 10% by weight of the total weight of the composition.

For the purpose of the present disclosure, the term "bioheteropolysaccharides" is intended to mean substances synthesized by fermentation of sugars by microorganisms. Bioheteropolysaccharides commonly have units chosen from mannose, glucose, glucuronic acid, and galacturonic acid units, which may be optionally acylated, in their chain.

Non-limiting mention may be made of the xanthan gums produced by the bacterium *Xanthomonas campestri* and the mutants and variants thereof.

These xanthan gums generally have a molecular weight ranging from 1 000 000 and 50 000 000.

Non-limiting mention may also be made of the *sclerotium* gums produced by *Sclerotium rolfsii*, the gellan gums produced by *Pseudomonas elodea* or *Sphingomonias*, the pullulan gums produced by *Aureobacidium pullulens*, the curdlan gums produced by the *Alcaligenes* of *Faecalis myxogenes* type, the xanthan gums produced by numerous organisms, including *Leuconostoc mesenteroides* and *Leuconostoc dextrantum*, the grifolan gums produced by *Grifola frondara*, the lentinan gums produced by *Lentinus edodes*, the schizophyllan gums produced by *Schizophyllum commine*, the spirulinan gums produced by *Spirulina sybsyla*, and the krestin gums produced by *Coriates versicolor*.

In at least one embodiment xanthan and *sclerotium* gums may be used. In another embodiment *sclerotium* gums may be used.

The at least one bioheteropolysaccharide is present in the dye composition in an amount ranging from 0.01% to 10% by weight of the total weight of the composition, such as ranging from 0.1%, and 4% by weight of the total weight of the composition.

The composition according to the present disclosure comprises at least one cationic surfactant that is well known, such as optionally polyoxyalkylenated primary, secondary, or tertiary fatty amine salts, quaternary ammonium salts, and mixtures thereof.

According to the present disclosure, the at least one cationic surfactant is nonpolymeric, i.e. the at least one cationic surfactant is not obtained by polymerization of monomers other than alkylene oxides or by grafting of cationic groups onto existing natural pigments.

Non-limiting examples of fatty amines include alkylamidoamines, such as ($C_8$-$C_{30}$)alkylamido($C_1$-$C_6$)dialkylamines and stearamidopropyldimethylamine (Mackine 301 sold by MacIntyre).

Non-limiting examples of quaternary ammonium salts include those having formula (V):

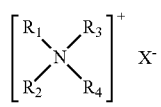     (V)

wherein $R_1$, $R_2$, $R_3$, and $R_4$, which may be identical or different, are each chosen from a linear or branched aliphatic radical comprising from 1 to 30 carbon atoms and an aromatic radical, such as aryl or alkylaryl. The aliphatic radicals may comprise heteroatoms, such as oxygen, nitrogen, sulphur, and halogens. The aliphatic radicals are chosen, for example, from ($C_1$-$C_{30}$)alkyl, alkoxy, ($C_2$-$C_6$) polyoxyalkylene, alkylamide, ($C_{12}$-$C_{22}$)alkylamido($C_2$-$C_6$)alkyl, ($C_{12}$-$C_{22}$)alkyl acetate, and hydroxyalkyl radicals, comprising from about 1 to 30 carbon atoms; and $X^-$ is an anion chosen from halides, phosphates, acetates, lactates, ($C_2$-$C_6$)alkyl sulphates, alkylsulphonates, and alkylaryl-sulphonates;

quaternary ammonium salts of imidazoline, for example, those of formula (VI):

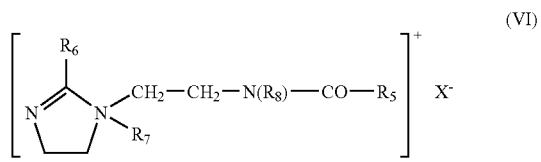     (VI)

wherein
$R_5$ is an alkenyl or alkyl radical containing from 8 to 30 carbon atoms, for example fatty acid derivatives of tallow or of coconut;
$R_6$ is chosen from a hydrogen atom, a $C_1$-$C_4$ alkyl radical, a $C_8$-$C_{30}$ alkenyl radical and a $C_8$-$C_{30}$ alkyl radical;
$R_7$ is a $C_1$-$C_4$ alkyl radical;
$R_8$ is chosen from a hydrogen atom and a $C_1$-$C_4$ alkyl radical; and $X^-$ is an anion chosen from halides, phosphates, acetates, lactates, alkyl sulphates, alkylsulphonates, and alkylarylsulphonates.

In at least one embodiment, $R_5$ and $R_6$ are a mixture of alkenyl or alkyl radicals containing from 12 to 21 carbon atoms, for example fatty acid derivatives of tallow; $R_7$ is methyl; and $R_8$ is hydrogen. Such products are, for example, Quaternium-27 (CTFA 2002), Quaternium-87 (CTFA 2002), and Quaternium-83 (CTFA 2002), which are sold under the name "Varisoft®" W575PG by the company Goldschmidt;

diquaternary ammonium salts of formula (VII):

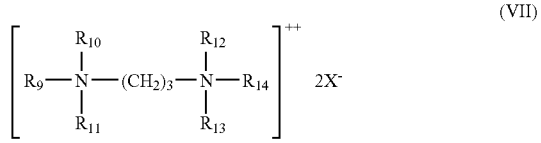     (VII)

wherein
$R_9$ is an aliphatic radical containing from 16 to 30 carbon atoms;
$R_{10}$, $R_{11}$, $R_{12}$, $R_{13}$, and $R_{14}$, which may be identical or different, are chosen from hydrogen and an alkyl radical containing from 1 to 4 carbon atoms; and
$X^-$ is an anion chosen from halides, acetates, phosphates, nitrates, ethyl sulphates, and methyl sulphates.

Such diquaternary ammonium salts comprise propanetallowediammonium dichloride;

quaternary ammonium salts comprising at least one ester function, such as those of formula (VIII):

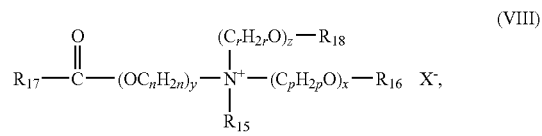     (VIII)

wherein:
$R_{15}$ is chosen from $C_1$-$C_6$ alkyl radicals and $C_1$-$C_6$ hydroxyalkyl or dihydroxyalkyl radicals;
$R_{16}$ is chosen from:
a radical

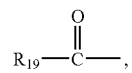, linear or branched, saturated or unsaturated $C_1$-$C_{22}$ hydrocarbon-based radicals $R_{20}$, and
a hydrogen atom,
$R_{17}$ is chosen from:
a radical

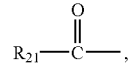, linear or branched, saturated or unsaturated $C_1$-$C_6$ hydrocarbon-based radicals $R_{22}$, and
a hydrogen atom,
$R_{19}$ and $R_{21}$, which may be identical or different, are chosen from linear or branched, saturated or unsaturated $C_7$-$C_{21}$ hydrocarbon-based radicals;
r, n, and p, which may be identical or different, are integers ranging from 2 to 6;
y is an integer ranging from 1 to 10;
x and z, which may be identical or different, are integers ranging from 0 to 10;
$X^-$ is a simple or complex, organic or inorganic anion;
with the provisos that the sum of x+y+z is from 1 to 15; that when x is 0, then $R_{16}$ is $R_{20}$; and that when z is 0, then $R_{18}$ is $R_{22}$.

The alkyl radical $R_{15}$ may be linear or branched. In at least one embodiment, the alkyl radical $R_{15}$ is linear.

In at least one embodiment, $R_{15}$ is chosen from methyl, ethyl, hydroxyethyl, and dihydroxypropyl radicals, and in a further embodiment, is chosen from methyl and ethyl radicals.

In at least one embodiment, the sum of x+y+z is from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it may contain from 1 to 3 carbon atoms.

In at least one embodiment, $R_{19}$ and $R_{21}$, which may be identical or different, are chosen from linear or branched, saturated or unsaturated $C_{11}$-$C_{21}$ hydrocarbon-based radicals. For example, $R_{19}$ and $R_{21}$ may be chosen from linear or branched, saturated or unsaturated $C_{11}$-$C_{21}$ alkyl and alkenyl radicals.

In at least one embodiment, x and z, which may be identical or different, are 0 or 1.

In at least one embodiment, y is 1.

In at least one embodiment, r, n and p, which may be identical or different, are 2 or 3, for example 2.

The anion $X^-$ is, for example, a halide (e.g., chloride, bromide or iodide) or a. $C_1$-$C_4$ alkyl sulphate, such as methyl sulphate. However, methanesulphonate, phosphate, nitrate, tosylate, an anion derived from an organic acid, such as acetate or lactate, or any, other anion that is compatible with the ammonium containing an ester function may also be used according to the present disclosure.

In at least one embodiment the anion $X^-$ is chloride or methyl sulphate.

In at least one embodiment, the ammonium salt is a compound of formula (VIII) wherein:
$R_{15}$ is a methyl or ethyl radical,
x and y are each 1;
z is 0 or 1;
r, n and p are each 2;
$R_{16}$ is chosen from:
a radical

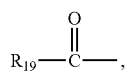

methyl, ethyl or $C_{14}$-$C_{22}$ hydrocarbon-based radicals, and a hydrogen atom;
$R_{18}$ is chosen from:
a radical

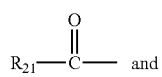 and a hydrogen atom;
$R_{19}$ and $R_{21}$, which may be identical or different, are chosen from linear or branched, saturated or unsaturated $C_{13}$-$C_{17}$ hydrocarbon-based radicals, such as from linear or branched, saturated or unsaturated $C_{13}$-$C_{17}$ alkyl and alkenyl radicals.

The hydrocarbon-based radicals are for example linear.

Non-limiting examples of compounds of formula (VIII) include the salts (such as chloride or methyl sulphate) of diacyloxyethyldimethylammonium, of diacyloxyethylhydroxyethylmethylammonium, of monoacyloxyethyldihydroxyethyl-methylammonium, of triacyloxyethylmethylammonium, of monoacyloxyethylhydroxyethyldimethylammonium, and mixtures thereof. The acyl radicals may contain from 14 to 18 carbon atoms and may be derived from a plant oil, such as palm oil or sunflower oil. When the compound contains several acyl radicals, these radicals may be identical or different.

These products are obtained, for example, by direct esterification of fatty acids or mixtures of fatty acids of plant or animal origin, or by transesterification of the methyl esters fatty acids or mixtures of fatty acids of plant or animal origin with optionally oxyalkylenated triethanolamine, triisopropanolamine, alkyldiethanolamine, or alkyldiisopropanolamine. This esterification is followed by a quaternization (salt formation) using an alkylating agent such as an alkyl halide (e.g., a methyl or ethyl halide), a dialkyl sulphate (e.g., dimethyl or diethyl sulphate), methyl methanesulphonate, methyl para-toluenesulphonate, glycol chlorohydrin, or glycerol chlorohydrin.

Such compounds are sold, for example, under the names Dehyquart® by the company Cognis, Stepanquat® by the company Stepan, Noxamium® by the company Ceca, and Rewoquat® WE 18 by the company Rewo-Goldschmidt.

The composition according to the present disclosure may, in at least one embodiment, contain a mixture of quaternary ammonium mono-, di-, and triester salts wherein the diester salts are present as the majority component by weight.

Non-limiting examples of mixtures of ammonium salts that may be used include the mixture containing 15% to 30% by weight of acyloxyethyldihydroxyethylmethylammonium methyl sulphate, 45% to 60% of diacyloxyethylhydroxyethylmethylammonium methyl sulphate, and 15% to 30% of triacyloxyethylmethylammonium methyl sulphate, the acyl radicals may contain from 14 to 18 carbon atoms and are derived from optionally partially hydrogenated palm oil.

The ammonium salts comprising at least one ester function described in U.S. Pat. Nos. 4,874,554 and 4,137,180 may also be used.

In at least one embodiment, the quaternary ammonium salts corresponding to formula (V) and formula (VIII) may be used in the compositions of the present disclosure. Non-limiting mention may be made of tetraalkylammonium chlorides, for instance dialkyl-dimethylammonium or alkyltrimethylammonium chlorides, wherein the alkyl radical contains from about 12 to 22 carbon atoms, in particular behenyltrimethylammonium, distearyldimethylammonium, cetyltrimethylammonium, or benzyldimethylstearylammonium chlorides, or alternatively, palmitylamidopropyltrimethylammonium chloride or stearamido-propyldimethyl(myristyl acetate)ammonium chloride corresponding to Quaternium-70 (CTFA 2002) sold under the name Ceraphyl® 70 by the company ISP.

The cationic surfactants that may be used in the composition of the present disclosure are chosen from quaternary ammonium salts, such as behenyltrimethylammonium chloride, cetyltrimethylammonium chloride, and Quaternium-83, Quaternium-87, behenylamidopropyl-2,3-dihydroxypropyldimethyl-ammonium chloride, palmitylamidopropyltrimethylammonium chloride, and stearamidopropyldimethylamine.

In the composition according to the present disclosure, the at least one cationic surfactant is present in an amount ranging from 0.01% to 10% by weight relative to the total weight of the composition, such as from 0.1% to 4% by weight relative to the total weight of the composition.

In at least one embodiment, the at least one cationic surfactant:at least one bioheteropolysaccharide weight ratio is greater than 1, such as from 1 to 10.

The at least one amphoteric surfactant contained in the composition of the present disclosure is chosen from surfactants that are known in the field of the direct dyeing of keratin fibers.

These amphoteric surfactants may be aliphatic secondary or tertiary amine derivatives, wherein the aliphatic radical is a linear or branched chain containing from 8 to 22 carbon atoms and containing at least one water-soluble anionic group (e.g., carboxylate, sulphonate, sulphate, phosphate or phosphonate). Non-limiting examples of amphoteric surfactants include $(C_8-C_{20})$alkylbetains, sulphobetains, $(C_8-C_{20})$alkylamido$(C_1-C_6)$alkyl-betains or $(C_8-C_{20})$alkylamido$(C_1-C_6)$alkylsulphobetains.

Among the amine derivatives, non-limiting mention may be made of the products sold under the name Miranol®, as described in U.S. Pat. Nos. 2,528,378 and 2,781,354, having the structures:

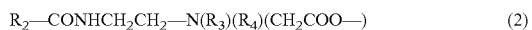

$$R_2—CONHCH_2CH_2—N(R_3)(R_4)(CH_2COO—) \quad (2)$$

wherein $R_2$ is chosen from an alkyl radical derived from an acid $R_2$—COOH present in hydrolyzed coprah oil, and from heptyl, nonyl, and undecyl radicals; $R_3$ is a beta-hydroxyethyl group; and $R_4$ is a carboxymethyl group; and

$$R_2—CONHCH_2CH_2—N(B)(C) \quad (3)$$

wherein
B is —$CH_2CH_2OX'$;
C is —$(CH_2)_z$—Y';
z is 1 or 2;
X' is chosen from —$CH_2CH_2$—COOH and a hydrogen atom;
Y' is chosen from —COOH and —$CH_2$—CHOH—$SO_3H$;
$R_2'$ is chosen from alkyl radicals of an acid $R_2$—COOH present in coprah oil or in hydrolyzed linseed oil, an alkyl radical, such as a $C_7$, $C_9$, $C_{11}$ or $C_{13}$ alkyl radical, a $C_{17}$ alkyl radical in its iso form, and an unsaturated $C_{17}$ radical.

These compounds are classified in the CTFA dictionary, 5th edition, 1993, under the name Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylampho-dipropionate, Disodium Caprylloamphodipropionate, Lauroamphodipropionic acid, and Cocoamphodipropionic acid.

A non-limiting example includes cocoamphodiacetate sold under the trade name Miranol® C2M concentrate by the company Rhodia.

Further non-limiting examples of amphoteric surfactants include alkylbetains, alkylamidoalkylbetains, and coamphodiacetate.

In at least one embodiment, the amphoteric surfactant is an alkylamidoalkylbetain.

The composition according to the present disclosure comprises the at least one amphoteric surfactant, which is present in an amount ranging from 0.01% to 20% by weight relative to the total weight of the composition, such as from 5% to 15% by weight relative to the total weight of the composition.

The composition of the present disclosure may comprise other surfactants, for example nonionic surfactants. Non-limiting examples of nonionic surfactants include those described in the "Handbook of Surfactants" by M. R. Porter, published by Blackie & Son (Glasgow and London), 1991, pp 116-178. Thus, they may be chosen from alcohols, alpha-diols, alkylphenols, or polyethoxylated, polypropoxylated or polyglycerylated fatty acids having a fatty chain containing, for example, from 8 to 18 carbon atoms, wherein the number of ethylene oxide or propylene oxide groups may be in the range from 2 to 50 and the number of glycerol groups may be in the range from 2 to 30. Non-limiting mention may also be made of copolymers of ethylene oxide and of propylene oxide, condensates of ethylene oxide and of propylene oxide on fatty alcohols; polyethoxylated fatty amides, having from 2 to 30 mol of ethylene oxide, polyglycerylated fatty amides comprising on average from 1 to 5 glycerol groups, such as from 1.5 to 4; oxyethylenated fatty acid esters of sorbitan having from 2 to 30 mol of ethylene oxide; fatty acid esters of sucrose, fatty acid esters of polyethylene glycol, alkylpolyglycosides, N-alkyl glucamine derivatives, amine oxides, such as $(C_{10}-C_{14})$alkylamine oxides or N-acylaminopropylmorpholine oxides. In at least one embodiment, alkylpolyglycosides or oxyalkylenated fatty alcohols are used.

The composition of the present disclosure may also contain at least one oxidation base, at least one coupler, or at least one of each conventionally used for oxidation dyeing.

Non-limiting examples of oxidation bases include para-phenylenediamines, bisphenylalkylenediamines, para-aminophenols, ortho-aminophenols, heterocyclic bases, and addition salts thereof.

The couplers may be chosen from, for example, meta-phenylenediamine couplers, meta-aminophenol couplers, meta-diphenol couplers, naphthalene couplers, heterocyclic couplers, and addition salts thereof.

When present, the oxidation bases and the couplers are each generally present in an amount ranging from 0.001% to 10% by weight relative to the total weight of the dye composition, such as from 0.005% to 6% by weight relative to the total weight of the dye composition.

The medium suitable for dyeing, also referred to as dye support, comprises water or a mixture of water and at least one organic solvent in order to solubilize the compounds that would not be sufficiently soluble in water. Non-limiting examples of solvents include organic solvents, such as $C_1-C_4$ lower alkanols, (e.g., ethanol and isopropanol); polyols and polyol ethers, (e.g., 2-butoxyethanol, propylene glycol, propylene glycol monomethyl ether), diethylene glycol monoethyl ether, and diethylene glycol monomethyl ether, and also aromatic alcohols (e.g, benzyl alcohol or phenoxyethanol), and mixtures thereof.

For the dyeing of human keratin fibers, the dyeing medium is an appropriate cosmetic medium.

The solvents may be present in an amount ranging from 1% to 40% by weight relative to the total weight of the dye composition. For example, the solvent may be present in an amount ranging from 5% to 30% by weight of the total weight of the dye composition.

The dyeing composition of the present disclosure may also contain various adjuvants conventionally used in compositions for dyeing the hair, such as anionic or zwitterionic surfactants or mixtures thereof, anionic, cationic, nonionic, amphoteric or zwitterionic polymers or mixtures thereof, thickeners other than the bioheteropolysaccharides described above, antioxidants, penetrating agents, sequestering agents, fragrances, buffers, dispersing agents, conditioning agents, such as, for example, modified or nonmodified, volatile or nonvolatile silicones, film-forming agents, ceramides, preserving agents, or opacifiers.

These adjuvants are present in an amount, for each of them, ranging from 0.01% to 20% by weight relative to the weight of the total composition.

Those skilled in the art will take care to select these optional additional compounds in such a way that the desired properties intrinsically associated with the oxidation dye composition of the present disclosure are not, or are not substantially, impaired by the additions envisaged.

The pH of the dye composition of the present disclosure ranges from 3 to 12, such as from 5 to 11.

The pH may be adjusted to the desired value by means of acidifying or basifying agents normally used in the dyeing of keratin fibers, or else by means of conventional buffer systems.

Non-limiting examples of acidifying agents include inorganic or organic acids, such as hydrochloric acid, orthophosphoric acid, sulphuric acid, carboxylic acids, such as acetic acid, tartaric acid, citric acid, or lactic acid, and sulphonic acids.

Non-limiting examples of basifying agents include aqueous ammonia, alkali metal carbonates, alkanolamines, such as mono-, di- and triethanolamines, and derivatives thereof, sodium hydroxide or potassium hydroxide, and the compounds of formula (III) below:

wherein W is a propylene residue optionally substituted with a hydroxyl group or a $C_1$-$C_4$ alkyl radical; $R_6$, $R_7$, $R_8$ and $R_9$, which may be identical or different, are chosen from a hydrogen atom, $C_1$-$C_4$ alkyl radicals, and $C_1$-$C_4$ hydroxyalkyl radicals.

The dye composition according to the present disclosure may be in various forms, such as in the form of liquids, creams or gels, or in any other form suitable for dyeing keratin fibers, for example, human keratin fibers, such as hair.

The present disclosure relates to a direct dyeing process comprising applying a composition as defined above to keratin fibers. After a leave-on time, the keratin fibers are rinsed, allowing colored fibers to appear. The leave-on time generally ranges from 3 to 50 minutes, such as from 5 to 30 minutes.

When the dye composition comprises an oxidation base and/or a coupler, the dye composition may also contain an oxidizing agent. The oxidizing agents conventionally used for the oxidation dyeing of keratin fibers are, for example, hydrogen peroxide, urea peroxide, alkali metal bromates, persalts such as perborates and persulphates, peracids and oxidase enzymes, such as peroxidases, 2-electron oxidoreductases, such as uricases, and 4-electron oxygenases, such as laccases. In at least one embodiment, hydrogen peroxide is used.

The oxidizing agent may be added to the composition of the present disclosure just at the moment of use, or it may be used from an oxidizing composition containing it, applied simultaneously with or sequentially to the composition of the present disclosure. The oxidizing composition may also contain various adjuvants conventionally used in compositions for dyeing the hair and as defined above.

The pH of the oxidizing composition containing the oxidizing agent is such that, after mixing with the dye composition of the present disclosure, the pH of the resulting composition applied to the keratin fibers ranges from 3 to 12, such as from 5 to 11. The pH may be adjusted to the desired value by means of acidifying or basifying agents normally used in the dyeing of keratin fibers and as defined above.

The composition which is finally applied to the keratin fibers may be in various forms, such as in the form of liquids, creams or gels, or in any other form suitable for dyeing keratin fibers, such as human hair.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

The following compositions were prepared, the amounts being given in amounts by weight, unless otherwise indicated.

Example 1

|  | Example 1 |
| --- | --- |
| 4-AMINO-3-NITROPHENOL | 0.145 |
| 3-NITRO-p-HYDROXYETHYLAMINOPHENOL | 1.35 |
| HC RED NO. 7 | 0.452 |
| HC RED NO. 3 | 0.18 |
| BASIC RED 51 | 0.04 |
| BASIC ORANGE 31 | 0.02 |
| CHLOROHEXIDINE DIHYDROCHLORIDE | 0.05 |
| METHYLPARABEN | 0.3 |
| SCLEROTIUM GUM | 1 |
| AMODIMETHICONE (and) TRIDECETH-6 (and) CETRIMONIUM CHLORIDE | 1.8 |
| PROPYLENE GLYCOL | 2 |
| CETEARYL ALCOHOL | 7 |
| BEHENTRIMONIUM CHLORIDE | 4 |
| COCAMIDOPROPYL BETAIN | 10 |
| ETHANOLAMINE | QS pH 6.7 |
| CITRIC ACID | |
| WATER | QS |

This composition was then applied to locks of natural grey hair containing 90% of white hairs, at ambient temperature. After 30 minutes, the locks of hair were rinsed with running water and then dried.

The locks were dyed in a relatively nonselective intense auburn shade. The hair was soft.

Example 2

|  | Example 2 |
| --- | --- |
| 3-METHYLAMINO-4-NITROPHENOXYETHANOL | 0.1 |
| DISPERSE VIOLET 1 | 0.12 |
| BASIC BROWN 16 | 0.03 |
| 2-NITRO-5-GLYCERYL METHYLANILINE | 0.25 |
| HC VIOLET NO. 1 | 0.042 |

-continued

| | Example 2 |
|---|---|
| HC BLUE NO. 2 | 0.7 |
| HC YELLOW NO. 7 | 0.02 |
| HC RED NO. 3 | 0.027 |
| HC YELLOW NO. 10 | 0.06 |
| HC BLUE NO. 14 | 0.5 |
| CHLOROHEXIDINE DIHYDROCHLORIDE | 0.05 |
| METHYLPARABEN | 0.3 |
| SCLEROTIUM GUM | 1 |
| AMODIMETHICONE (and) TRIDECETH-6 (and) CETRIMONIUM CHLORIDE | 1.8 |
| PROPYLENE GLYCOL | 2 |
| CETEARYL ALCOHOL | 7 |
| BEHENTRIMONIUM CHLORIDE | 4 |
| COCAMIDOPROPYL BETAIN | 10 |
| ETHANOLAMINE | QS pH 9.6 |
| CITRIC ACID | |
| WATER | QS |

This composition was then applied to locks of natural grey hair containing 90% of white hairs, at ambient temperature. After 30 minutes, the locks of hair were rinsed with running water and then dried.

The locks were tinted in a relatively nonselective light chestnut shade of good intensity. The hair was soft.

Example 3

| | Example 3 |
|---|---|
| 4-AMINO-3-NITROPHENOL | 0.085 |
| 3-METHYLAMINO-4-NITROPHENOXYETHANOL | 0.021 |
| BASIC YELLOW 57 | 0.1 |
| HC RED NO. 3 | 0.017 |
| HC YELLOW NO. 9 | 0.035 |
| HC ORANGE NO. 2 | 0.61 |
| CHLOROHEXIDINE DIHYDROCHLORIDE | 0.05 |
| METHYLPARABEN | 0.3 |
| SCLEROTIUM GUM | 1 |
| AMODIMETHICONE (and) TRIDECETH-6 (and) CETRIMONIUM CHLORIDE | 1.8 |
| PROPYLENE GLYCOL | 2 |
| CETEARYL ALCOHOL | 7 |
| BEHENTRIMONIUM CHLORIDE | 4 |
| COCAMIDOPROPYL BETAIN | 10.53 |
| ETHANOLAMINE | QS pH 6.7 |
| CITRIC ACID | |
| WATER | QS |

This composition was then applied to locks of natural grey hair containing 90% of white hairs, at ambient temperature. After 30 minutes, the locks of hair were rinsed with running water and then dried.

The locks were tinted in a relatively nonselective intense golden shade. The hair was soft.

For each of these examples, the same type of result was obtained when the 1% of *sclerotium* gum is replaced with 1% of xanthan gum.

What is claimed is:

1. A composition for dyeing keratin fibers, comprising
at least one direct dye,
at least one bioheteropolysaccharide,
at least one cationic surfactant, and
at least one amphoteric surfactant,
wherein,
the at least one bioheteropolysaccharide is chosen from *sclerotium* gums,
the at least one amphoteric surfactant is chosen from betaines, and
the weight ratio of the at least one cationic surfactant to the at least one bioheteropolysaccharide is greater than 1.

2. The composition according to claim 1, wherein the at least one direct dye is chosen from neutral, acidic, or cationic nitrobenzene direct dyes, neutral, acidic, or cationic azo direct dyes, quinone direct dyes, azine direct dyes, triarylmethane direct dyes, indoamine direct dyes, and natural direct dyes.

3. The composition according to claim 1, wherein the at least one direct dye is present in an amount ranging from 0.001% to 20% by weight of the total weight of the composition.

4. The composition according to claim 3, wherein the at least one direct dye is present in an amount ranging from 0.005% to 10% by weight relative to the total weight of the composition.

5. The composition according to claim 1, wherein the at least one bioheteropolysaccharide is present in an amount ranging from 0.01% to 10% by weight relative to the total weight of the composition.

6. The composition according to claim 5, wherein the at least one bioheteropolysaccharide is present in an amount ranging from 0.1% to 4% by weight, relative to the total weight of the composition.

7. The composition according to claim 1, wherein the at least one cationic surfactant is chosen from primary, secondary, or tertiary fatty amine salts, quaternary ammonium salts, and mixtures thereof.

8. The composition according to claim 5, wherein the at least one cationic surfactant is chosen from primary, secondary, or tertiary fatty amine salts, quaternary ammonium salts, and mixtures thereof.

9. The composition according to claim 5, wherein the at least one cationic surfactant is chosen from behenyltrimethylammonium chloride, cetyltrimethylammonium chloride, quaternium-83, quaternium-87, behenylamidopropyl-2,3-dihydroxypropyldimethylammonium chloride, palmitylamidopropyltrimethylammonium chloride, and stearamidopropyldimethylamine.

10. The composition according to claim 1, wherein the at least one cationic surfactant is present in an amount ranging from 0.01% to 10% by weight relative to the total weight of the composition.

11. The composition according to claim 10, wherein the least one cationic surfactant is present in an amount ranging from 0.1% to 4% by weight relative to the total weight of the composition.

12. The composition according to claim 1, wherein the at least one amphoteric surfactant is chosen from alkylbetains, alkylamidoalkylbetains, and coamphodiacetate.

13. The composition according to claim 1, wherein the at least one amphoteric surfactant is present in an amount ranging from 0.01% to 20% by weight relative to the total weight of the composition.

14. The composition according to claim 13, wherein the at least one amphoteric surfactant is present in an amount ranging from 5% to 15% by weight relative to the total weight of the composition.

15. The composition according to claim 1, further comprising at least one oxidation base, at least one coupler, and/or mixtures thereof.

16. The composition according to claim 1, further comprising at least one oxidizing agent.

17. A process for dyeing keratin fibers comprising applying to said keratin fibers a dyeing composition comprising
at least one direct dye,
at least one bioheteropolysaccharide,
at least one cationic surfactant, and
at least one amphoteric surfactant,
for a period of time sufficient to develop a desired coloration,
wherein
the at least one bioheteropolysaccharide is chosen from *sclerotium* gums,
the at least one amphoteric surfactant is chosen from betaines, and
the weight ratio of the at least one cationic surfactant to the at least one bioheteropolysaccharide is greater than 1.

* * * * *